United States Patent [19]

Marx

[11] 4,027,666
[45] June 7, 1977

[54] SEMIRIGID COUNTERFORCE BRACE

[76] Inventor: Alvin J. Marx, 315 College Road, Bronx, N.Y. 10471

[22] Filed: Sept. 26, 1975

[21] Appl. No.: 617,144

[52] U.S. Cl. .................. 128/165; 128/DIG. 15; 273/189 R

[51] Int. Cl.² .......................... A61F 13/00

[58] Field of Search .......... 128/165, 169, 78, 87 R, 128/157, 327, DIG. 15; 273/189 R, 189 A; 2/3 R, 2, 44, 45, 16

[56] References Cited

UNITED STATES PATENTS

| | | | |
|---|---|---|---|
| 2,646,797 | 7/1953 | Scholl | 128/165 |
| 2,687,129 | 8/1954 | Talkish | 128/78 |
| 3,297,026 | 1/1967 | Van Pelt | 128/165 X |
| 3,658,345 | 4/1972 | Siggson | 273/189 A |
| 3,700,245 | 10/1972 | Nannini | 273/189 A |
| 3,786,804 | 1/1974 | Lewis | 128/DIG. 15 |
| 3,789,842 | 2/1974 | Froimson | 128/165 |
| 3,831,467 | 8/1974 | Moore | 128/165 X |
| 3,877,426 | 4/1975 | Nirschl | 128/165 |
| 3,921,222 | 11/1975 | Hollman | 128/78 X |

FOREIGN PATENTS OR APPLICATIONS

| | | | |
|---|---|---|---|
| 528,044 | 1/1957 | Belgium | 128/87 R |

Primary Examiner—Clifford D. Crowder

[57] ABSTRACT

An improved semirigid counterforce brace adapted for application on a user's forearm helps prevent and provides relief during tennis play of tendonitis of the conjoined tendon of the extensor communis and extensor carpi radialis brevis at the insertion into the lateral epicondyl, a condition commonly referred to as "tennis elbow". The brace includes a semirigid, perforated, fluid passing outer plastic backer and inner porous strap, e.g., of a fabric laminated with an open pore foamed urethane, and a strap attached to the brace and adapted to wrap around the subject's forearm, pass through a loop disposed near, but not at, one end of the outer surface of the backer sheet, and to be secured in place by cooperating fasteners, e.g., cooperating hook and eye [VELCRO (tm)] type fasteners.

6 Claims, 3 Drawing Figures

SEMIRIGID COUNTERFORCE BRACE

DISCLOSURE OF THE INVENTION

This invention relates to athletic/medical apparatus and, more specifically, to an improved semirigid counterforce brace permitting tennis play when a subject suffers from so called tennis elbow and for preventing this condition.

Tennis elbow is a tendonitis of the conjoined tendon of the extensor communis and extensor carpi radialis brevis at the insertion into the lateral epicondyl. Additionally there may be inflammation of the aponeurotic space and lateral collateral ligament. Stated in more general terms, tennis elbow is an inflammation of the tendon that connects the extensors of the forearm with the lateral part of the elbow.

This condition results from excessive (too rapid, too forceful, or too frequent) stretching of the tendon of the forearm. It typically and frequently occurs in people over 35, generally believed to affect 50% of tennis players over that age.

Tennis elbow usually resolves spontaneously after a period of rest (1–6 months). Local injection of steroids will also relieve symptoms, although this therapy has on occasion resulted in a torn tendon. A third method of treatment that will allow the patient to continue to play tennis is a brace placed below the elbow. Analgesics and heat give some symptomatic relief. If the condition is not treated the patient may have too much pain to play tennis. Continued ignoring of the pain may lead to calcification and prolonged or chronic pain.

To prevent this condition and permit continued tennis play during the above identified tendonitis or, more commonly, tennis elbow condition, varying forms of tennis braces have heretofore been employed as above noted. Such counterforce braces are typically located about two inches below the elbow and firmly wrapped around the subject's forearm. The exact physiological operation of the counterforce brace is not fully understood but, it is generally hypothecated that the brace reduces the force on the extensor tendon of the elbow when a ball is struck, presumably acting as the counterforce for the operative forearm muscles in place of the aggravated tendon.

However, such prior arm braces have not been entirely satisfactory. As a generality, they do not fully provide the requisite bracing action and they suffer from one or more of the deficiencies of (1) being difficult to apply; (2) being unsightly; (3) accumulating perspiration under the forearm wrapping, also causing local heat generation by obviating perspiration evaporation; (4) being easily soiled and generally unwashable; (5) requiring relatively frequent replacement; (6) slipping, and or abrading the skin; (7) causing an irritating and painful skin pinching where buckles eyelets, or like loops have been employed; and (8) being difficult to adjust proper tension.

It is thus an object of the present invention to provide an improved semirigid counterforce brace.

More specifically, it is an object of the present invention to provide a forearm counterforce brace which substantially obviates the above noted deficiencies.

The above and other objects of the present invention are realized in an improved semirigid counterforce brace which includes a semirigid plastic apertured backer sheet in generally circular form. An open pore plastic foam strip is secured to the inner surface of the plastic backer and completely covers the inner surface of the backer to not expose any of the plastic backer to the forearm. An additional section of open pore foam with reinforcing material, such as non-woven fabric, bonded to both sides of the foam is secured to the plastic backer sheet to permit a complete wrapping about a subject's forearm.

In use, the composite improved counterforce brace is very readily slipped onto a subject's forearm slightly below the elbow, the additional portion of the reinforced plastic foam strap passing through a loop-like aperture on the outer part of the semirigid backer and looping back on itself such that the end portion of the strap is secured in place, as by loop and eye (e.g., VELORO type) mating fastener strips. The counterforce brace above described provides a rigid counterforce point to relieve strain on the lateral epicondyl during tennis play; is readily applied; provides ready perspiration elimination passing through the foamed strip and backer sheet apertures; provides additional cushioning by conforming to the contours of the forearm; remains firmly in place during use; is easily adjusted to the desired tightness; and otherwise provides substantial improvement vis-a-vis heretofore existing counterforce braces with respect to the considerations and deficiencies above discussed.

The above and other features of the present invention will become more clear from the following description of a specific illustrative counterforce brace described hereinbelow in conjunction with the accompanying drawing in which.

Figure 1:
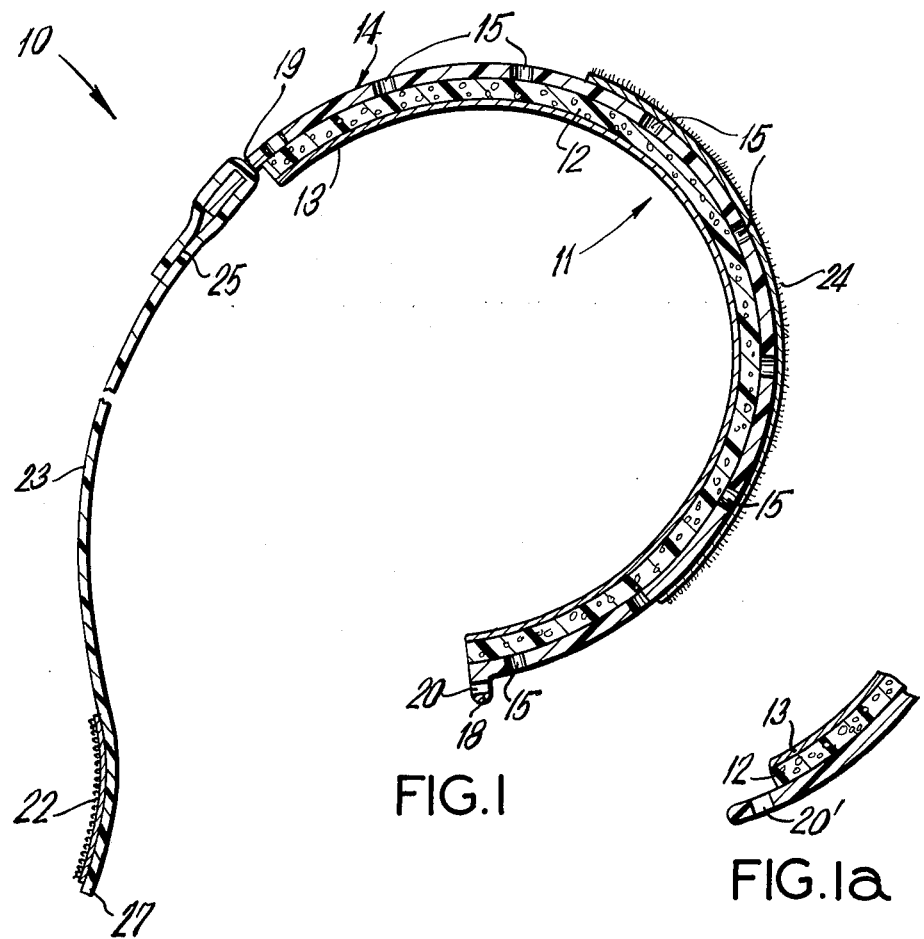
FIG. 1 is a cross-sectional view of a semirigid counterforce brace, in an unapplied orientation.

Referring now to the drawing, there is shown an improved semirigid counterforce brace employing the principles of the present invention, finding general utility for relieving the tennis elbow condition so prevalent in aging tennis players over 35. The brace is formed of a semirigid rounded plastic outer backer layer 14 formed with a plurality of apertures 15 for ventilation and the elimination of perspiration. The outer semirigid backer material may be formed of any desired plastic material, such as nylon, polyethylene and polypropylene being considered particularly advantageous. Disposed about the inner surface of the outer layer 14 is a laminated strip 11 which includes a relative soft, fluid (perspiration) passing material 12 such as an open pore urethane foam, and a fabric 13 (woven or nonwoven) which acts as a perspiration wicking agent.

In accordance with one aspect of the present invention, the inner surface of lamination 11 operates with a reinforced strap 23 to form a complete circumferential contact with the subject's forearm. The strap 23 may comprise cloth, or a laminate as of open pore foam and cloth, or similar material. The strip 11 is adapted to be at least as wide as the backer strip 14, while the reinforced strap 23 is somewhat narrower to freely pass through a loop aperture 20 in or attached to backer 14. The strap 23 is fastened to the backer 14 by passing through a slot 19 and being wrapped around to meet on itself and be permanently connected by means of sewing 25 or other bonding technique.

Figure 1A:
FIG. 1A is a cross-sectional view of an end portion of an alternate brace construction.
Figure 2:
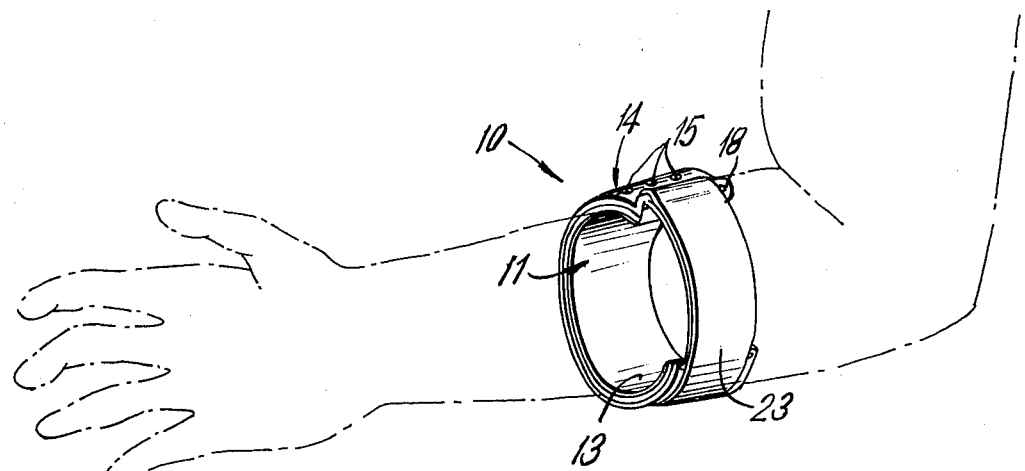
FIG. 2 depicts the composite counterforce brace as applied to a subject's forearm.

The member 14 includes a projecting portion 18 which defines an enclosed loop aperture 20 (FIG. 1). The loop 18-20 may be completely formed when the member 14 is prepared (e.g., molded) or, alternatively, the requisite loop aperture 20 may be formed by a separately attached bar. To this end, the separately attached bar may be in the form of a rectangle with projections such that its ends pass into retaining apertures formed in the outer member 14 and are permanently joined to member 14. In any event, the free end 27 of the strap 23 12 passes through the aperture 20. Alternatively (FIG. 1A), slot 20' may be directly formed into the backer 14.

The composite counterforce brace shown in the drawing is simply affixed in position by the subject who simply passes his arm through the slack loop formed by the inner laminate strip 11 and strap 23 (assuming that the strap end 27 has already passed through the aperture 20) or alternatively, clamps the semirigid brace 14-12 over his arm and thereafter inserts the strap end 27 through the aperture 20. In either case, the subject simply pulls the end 27 of the strap 23 back upon itself until the desired degree of tightness has been achieved.

To lock the counterforce brace in place, one part 22 of a mating fastener system is attached about the outer surface of the strap 23 about the end 27, the element 22, for example, forming one part of a hook and eye rapid attachment, quick release system well known to those skilled in the art and sold, for example, under the trademark VELCRO. A mating strip 24 to the element 22 is located on the outer surface of the semirigid plastic material 14.

In use, the composite improved semirigid counterforce brace is thus readily applied in the manner above described, and provides a firm, reliable prophylactic obviating aggravation of the subject's tendonitis condition and permitting continued tennis play notwithstanding such condition.

The above described arrangement is merely illustrative of the principles of the present invention. Numerous modifications and adaptations thereof will be readily apparent to those skilled in the art without departing from the spirit and scope of the present invention.

What is claimed is:

1. A counterforce brace adapted for application over a subject's forearm entirely below the elbow comprising semirigid curved backer sheet means having a plurality of perspiration eliminating apertures therein, the width of said backer sheet means being less than its length in the forearm circumferential direction, said circumferential length being the greater part of a subject's forearm circumference, a porous perspiration passing inner strip disposed about the inner surface of said backer sheet means, slot means formed within said backer sheet means at one end thereof, strap means attached to said semirigid curved backer sheet at said slot means at said one end of said backer sheet means, loop means integrally formed within said semirigid backer sheet means about the outer surface thereof near the other end of said semirigid backer sheet means, said loop being adapted to receive the other end of said strap means, and brace securing means comprising mating first and second portions, said first portion of said brace securing means being affixed to the outer surface of said strap means about the end thereof remote from said slot means and the second portion of said brace securing means being secured to the outer surface of said semirigid backer sheet means.

2. A combination as in claim 1 wherein said inner strip comprises a laminate including an open pore foam and a cloth wicking agent.

3. A combination as in claim 2 wherein said open pore foam comprises an open pore urethane foam.

4. A combination as in claim 1 wherein said semirigid outer backer sheet is formed of a material selected from the group consisting of nylon, polyethylene or polypropylene.

5. A combination as in claim 1 wherein said first and second portions of said brace securing means respectively comprise hook and eye fastener segments.

6. A combination as in claim 1 wherein said inner strip comprises a laminate comprising foam and cloth.

* * * * *